United States Patent [19]
Pardikes

[11] Patent Number: 5,323,017
[45] Date of Patent: Jun. 21, 1994

[54] LOW/HIGH ALARM FOR POLYMER FLOW

[76] Inventor: Dennis G. Pardikes, 12811 S. 82nd St., Palos Park, Ill. 60464

[21] Appl. No.: 42,148

[22] Filed: Apr. 2, 1993

[51] Int. Cl.$^5$ ................................................ G01N 5/06
[52] U.S. Cl. ..................................... 250/573; 356/442
[58] Field of Search ............... 250/573, 574, 576; 356/442; 340/619, 606; 210/87, 94, 95

[56] References Cited

U.S. PATENT DOCUMENTS 4,213,454 7/1980 Shim ............................ 340/619
4,629,903 12/1986 Gicobbe et al. ............... 250/513

Primary Examiner—David C. Nelms
Assistant Examiner—K. Shami
Attorney, Agent, or Firm—Laff, Whitesel, Conte & Saret

[57] ABSTRACT

A low cost optical sensor using ordinary non-coherent light reads the polymer content of a processed polymer solution and gives a go/no-go signal in response thereto. The system shuts down in response to the no-go signal. There are no moving parts to pick up or be fouled by polymer.

16 Claims, 1 Drawing Sheet

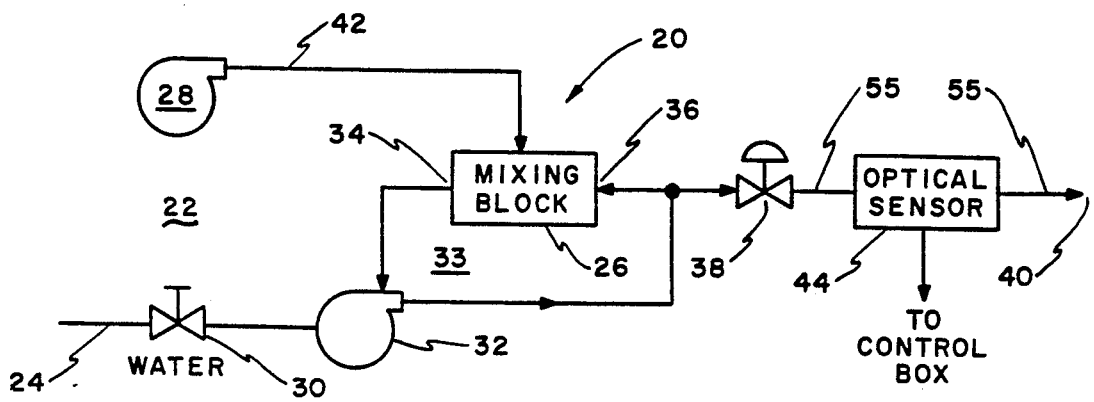
FIG. 1
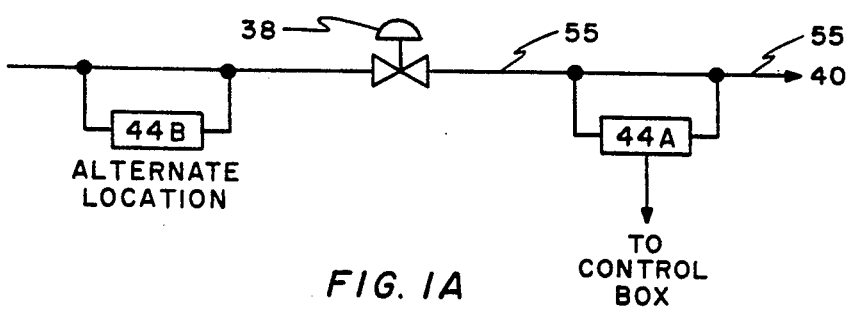
FIG. 1A
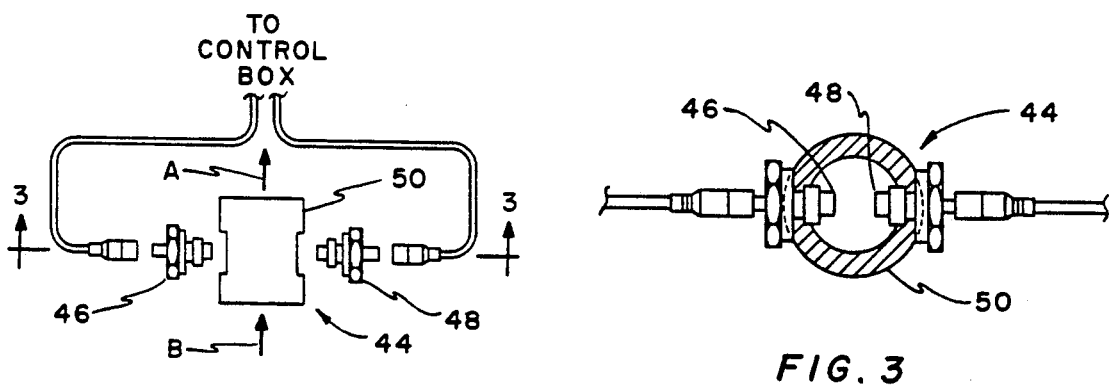
FIG. 2
FIG. 3
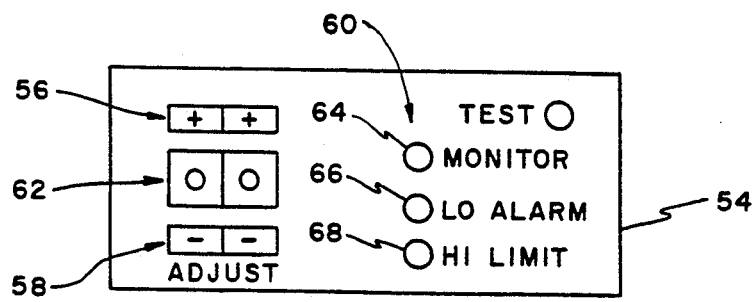
FIG. 4

LOW/HIGH ALARM FOR POLYMER FLOW

This invention relates to analyzer means for monitoring and giving a low/high alarm relating to the concentration of a polymer solution as it is being blended or activated by a polymer processing system, and more particularly to a sensor for detecting the concentration of polymer by use of transmission of light so that no moving mechanical parts must touch this solution.

Another of my inventions, shown in a co-pending patent application Ser. No. 08/012,412, filed Feb. 16, 1993, shows a similar sensor using a laser light source. That laser light sensor gives an analog signal which may be fed back to automatically control the system. Thus, a number of micro-adjustments may be made on the system operations in response to the analog signal so that the processed polymer output may be held within very narrow limits.

This laser controlled sensor and automatic system control is relatively expensive; however, the cost may be more than justified for some products such as those requiring high quality, such as the polymers used by the paper making industry. On the other hand, other industries, such as waste disposal, do not require such a high quality polymer or such a precisely controlled product. For this latter kind of product, it is enough if the system merely responds to go/no-go conditions and shuts itself down if the processed polymer falls outside of a predetermined range. Therefore, there is also a need for a relative low cost sensor.

For the latter product, there is no need for either a process analog output signal or constant system adjustments. The sensor only has to respond to high and low limits of polymer concentration which indicates that the product is in the desired range required of a final processed polymer. The system shuts itself down and gives an alarm if processing moves outside of this range. Then, the operator makes any manual adjustment that may be required and restarts the system. This kind of sensor costs only a minor fraction of the cost of the laser sensor with its analog output and automatic response thereto.

Accordingly, the inventive system operates around some selected midpoint and shuts itself down if the output product drifts out of range, giving an alarm indication of whether the drift is above or below the set limits.

In the past, many devices which have been used to provide such polymer flow alarms, have required high maintenance costs and have been subject to frequent interruptions of production. In greater detail, a polymer has a long chain molecule comprised of varying chemical groups that impose cationic or anionic charges which neutralize particle charges on molecules suspended in an aqueous medium in order to control coagulation and flocculation. In many cases, the polymer must first be processed in order to be useful in its role as a charge de-stabilizer. This involves a processing system which introduces the polymer to water, and blends them into a homogeneous solution. If required, the processing also provides the shear which is necessary to strip away an oil carrier associated with various types of polymer known as emulsions and dispersions.

Until now, most polymer flow alarms have been used for monitoring a neat polymer stream before it is mixed with water. These alarms often used both flat and rotary flow vanes, thermal sensing elements, or level devices. However, these approaches are not desirable because each system has parts which come in to contact with the polymer itself. In its neat form, especially emulsion and dispersion forms, polymer has an oily viscous coating that deposits itself tenaciously on everything which comes into contact with it. Mechanical level floats and flow vanes, and the like, often become jammed or otherwise ineffective as they are fouled and contaminated by these deposits. When thermal sensing devices sense flow by reading changes of temperature between elements which become coated with polymer, there is an insulating effect so that the sensing element cannot accurately read the temperature values. This thermal sensing type of flow alarm requires frequent servicing and is often impossible to calibrate at the lower flow ranges.

Accordingly, an object of this invention is to provide new and improved means for and methods of monitoring the concentration and flow of a polymer in a polymer processing system. In particular, an object is to monitor the flow after an oil carrier has been stripped away from emulsions and dispersions. In this connection, an object is to detect the condition of the polymer flow without resort to any moving parts.

In keeping with an aspect of this invention, the concentration analyzer uses a light source which shines through a polymer solution to an opposed photocell. The amount of light reaching the photocell indicates whether the polymer solution exiting the polymer processing system is within an acceptable range centered on a preset level of activation and concentration. An operator can determine the desired solution concentration and set the alarm level required to shut down the processing system and give an alarm if the desired concentration is not maintained.

The attached drawing shows a preferred embodiment of the invention in which:

FIG. 1 schematically shows a polymer processing system with the inventive sensor coupled in series with a line at the output thereof;

FIG. 1A shows an alternative location of the sensor in parallel with a line at the output of the system;

FIG. 2 is an exploded view of the inventive sensor cell;

FIG. 3 (taken along line 3—3 of FIG. 2) shows a cross section of an assembled sensor cell; and FIG. 4 is a front elevation of a control panel on a sensor control box.

Polymer processing systems may take many forms, an exemplary one 20 of which is shown in FIG. 1. The system of FIG. 1 is an elementary showing of a polymer processing system sold under the trademark "AnCAT" by Norchem Industries, 760 North Frontage Road, Willowbrook, Ill. 60521.

A source 22 of neat polymer and a source 24 of water is connected to a mixing block 26. The neat polymer source is coupled to mixing block 26 via pump 28. The water source is coupled to block 26 via a valve 30 and pump 32. The water and polymer are mixed at a relatively high pressure in mixing block 26, with a certain percentage of the mixed polymer and water being fed back through a closed loop 33 including block 26, outlet 34, pump 32 to mixing block inlet 36. Another percentage of the mixture is diverted through a pressure regulator 38 to a system output 40.

The "AnCAT" polymer processing system uses a combination of three technologies or elements which merge in a totally un-obvious fashion. These three elements are used for making or "breaking" emulsions. The first element is provided by the pressure regulator 38 which creates or breaks an emulsion by subjecting the pressurized polymer and water solution in feedback loop 33 to a sudden and violent drop in pressure as the solution passes through an orifice in regulator 38. In order to achieve satisfactory emulsification conditions, an exemplary system causes from 1 to 100 psi pressure drop through a small orifice. The second element subjects the solution to a high flow and pressure condition through a static or motionless mixer in mixing block 26. In order to achieve satisfactory emulsification conditions, the exemplary system preferably uses flow rates greater than 2.5 ft/sec and pressure differentials in excess of 10 psi over mixer elements of several inches or more in length. The combination of variables governing the static mixer in mixing block 26 must create Reynold's numbers sufficient for satisfactory mixing. The third element for creating or breaking an emulsion subjects the solution to extreme three dimensional, hydrodynamic shear which is created within the chamber of a centrifugal pump/mixer 32. In order to achieve satisfactory emulsifying conditions the pump/mixer combination requires an extraordinary input of energy, usually referred to as horsepower, as compared to the horse power normally to be expected.

Thus, the essence of the "AnCAT" technology is the apparatus and method of making o breaking emulsions using these three elements in a unique combination. The net effect is a synergism of the elements shown in FIG. 1, which perform in combination better and more effectively than any single element or combination of those elements prior to the disclosure of the invention.

Heretofore, equipment for monitoring the flow of polymer in the system would have been connected into neat polymer line 42 between the pump 28 and mixing block 26. There, the flow rate would most likely have been measured by some kind of mechanical device, such as a turbine which is turned by the flowing polymer stream or a thermal type sensor.

The inventive system places an optical sensor 44 at the output of the system. Thus, the inventive device does not look at only the neat polymer flow. It takes its readings from the diluted polymer solution. The advantages over the prior art are many. First, by the time that the alarm takes its reading on the activated polymer solution, the oil film has been thoroughly stripped away and emulsified. Water has diluted the polymer by an average of 100 to 300 fold. Second, the volumetric flow rate of the polymer is no longer a factor because the inventive sensor is optically scanning the polymer solution and does not have to rely on a minimum flow rate in the neat polymer stream. Thus, the invention gives more accurate readings, with less maintenance required. In fact, it has been found that this new and unique method can accurately and reliably sense polymer in a water base down to one part in one thousand. Compared to prior art sensing methods, this optical sensing is in the order of ten times more sensitive than the traditional flow alarms.

This new and improved optical sensing device is virtually maintenance free because the flow cell in the polymer solution line is reading the polymer solution as it leaves the processing system. The significantly higher velocities of the polymer solution flow rate associated with this placement at the system output constantly purge the sense cell with 99-299 parts of water to one part polymer and by velocities which are high enough to keep the cell and its associated components clean.

The inventive sensor device 44 (FIGS. 2, 3) incorporates a flow cell with a light emitter 46 and photocell detector 48 mounted in an opposed configuration, within a flow chamber housing 50. The light emitter 46 provides an ordinary visible light source. The photocell detector 48 includes a CdS photocell. In FIG. 2, arrows A, B show the direction in which the solution flows through housing 50. The "+" in FIG. 3 represents the tail feathers of an arrow indicating the direction of polymer solution flow.

These assemblies are, in turn, connected to a power supply and signal conditioner at a control panel 52 which is preferably mounted in a nearby separate enclosure. The flow cell sensor 44 is mounted in a suitable location where it can monitor the mixed polymer and water solution while the system is running. In FIG. i, sensor 44 is coupled in series with output line 55 to monitor 100 percent of the outflow. In FIG. 1A, the sensor (44A position) is in parallel with output line 55 to monitor a sample of the outflow. An alternate position places the sensor (44B) upstream of the valve 38.

In the flow cell, the intensity of the light produced at source 46, which is received at the detector assembly 48, varies inversely with the concentration of the polymer solution flowing within housing 50. In detector 48, the resistance of a CdS photocell is inversely variable with the intensity of the light falling on it. Due to these two inverse relationships acting in conjunction with each other, the output resistance of the photocell becomes directly proportional to the concentration of the polymer solution.

The signal conditioner for the photocell output and power supply are mounted in a single housing 54 (FIG. 4) with user accessible controls 56, 58 for setting the desired polymer concentration values and alarm lights 60 for signalling when the polymer concentration is out of an acceptable range. As an example, the invention provides the operator with a digital display signal 62 that may be set to command an arbitrary concentration value.

In greater detail, FIG. 4 shows two digital positions 62 which may display any numbers or other symbols selected by the user. Of course, any suitable number of digital positions may be provided. Over each digital position is an individually associated push button 56 which adds one count to the displayed digit. Under each digital position is a similar individually associated push button 58 which subtracts one count from the displayed digit. Thus, by pushing the push buttons 56, 58, the user may select any suitable digital display.

Three lights 60 are provided. One monitor light 64 indicates when the system is switched on and the sensor 44 is actively monitoring the polymer processor system. Alarm light 66 lights to give an alarm when the polymer concentration in the outflow drops below a certain "low" level. Alarm light 68 lights when the polymer concentration in the outflow exceeds a selected high level. The function of the sensor 44 is to enable an operator to adjust the polymer processing system so that it is operating at a mid-range level with neither of the alarm lights 66, 68 lit.

The operator starts the polymer processing system (FIG. 1) and manually adjusts the push buttons of FIG. 4 to display a digital setting which gives a reading of zero at a time when the neat polymer source 28 is turned off and only water is flowing from source 32 though the unit. The operator increases the digital setting displayed at 62 until an alarm trips which is indicated by a lit low level panel light 66. The number displayed at this digital setting indicates a baseline value for water only. The operator notes the digital setting at 6 resulting from the flow of water only.

Then, the operator turns on the neat polymer pump 28 (FIG. 1) and adjusts the pump speed for the desired solution concentration. Next, the operator increases the digital setting until the low level alarm lamp is again lit. This displayed digital setting is the low concentration of polymer threshold value.

By adding the displayed digital setting at the water baseline value to the displayed digital setting at the low concentration polymer threshold value and dividing by two, the user knows a "set point," where the polymer concentration deviates approximately 50 percent from the set point. Then, the digital setting may be reset to this new value which is a mid-range alarm point. However, the operator may also select any suitable point between the water baseline and the polymer threshold which meets his particular needs. An associated microprocessor or logic circuit may be programmed or designed to give a high limit alarm at a predetermined differential level above the set point.

The system shuts down simultaneously with the lighting of either of the alarm lights 66, 68.

The instructions to the user are as follows:

1. With the injection module set to its lowest speed, adjust the push button setting until the low polymer alarm light just comes on. Note this setting.
2. Adjust the injection module speed control until the polymer processing unit is producing the desired polymer concentration. Increase the pushbutton setting until the low polymer alarm light just comes on. Note this setting.
3. Add the two numbers noted in steps 1 and 2 and divide the sum by two.
4. Adjust the push button setting to display this value.

Those who are skilled in the art will readily perceive how to modify the invention. Therefore, the appended claims are to be construed to cover all equivalent structures which fall within the true scope and spirit of the invention.

The claimed invention is:

1. An optical sensor for a polymer processing system for processing neat polymer by mixing it with an electrolyte and delivering the resulting solution to an output, said optical sensor comprising means for use at said output for detecting the relative amount of polymer in the solution, said optical sensor further comprising a housing through which said polymer solution may flow, a non-coherent visible light source on one side of said housing, a photocell means on the opposite side of said housing for detecting light from said source after it has passed through said housing and any polymer solution that may be flowing therein, and means responsive to said detected light falling on said photocell means for giving high and low alarm signals when the relative amount of polymer in said solution is outside a predetermined range.

2. The sensor of claim 1 and means responsive to said high and low alarm signals for shutting down said polymer processing system.

3. The sensor of claim 1 and means responsive to said high and low alarm signals for indicating a need to shut down said polymer processing system.

4. The sensor of claim 1 wherein said sensor housing is adapted to be coupled in series with an output line carrying said polymer solution.

5. The sensor of claim 1 wherein said sensor housing is adapted to be coupled in parallel with an output line carrying said polymer solution.

6. A polymer processing system comprising a mixing block, a source of neat polymer coupled to said mixing block, a source of an electrolyte fluid coupled to said mixing block, a feed back loop for recirculating a predetermined portion of a solution formed by a mixture of said neat polymer and electrolyte, means for pressurizing said mixing block and feed back loop for subjecting said solution to a relative high pressure, means for diverting a complementary position of said solution to an output line, means for suddenly and substantially dropping said pressure in said diverted solution to a relatively low pressure, sensor means coupled to monitor a polymer content of said diverted solution after said pressure drop, said sensor comprising means for detecting an amount of light shining through and emerging from said diverted solution, and means for giving an alarm on a go/no-go basis responsive to said sensor means receiving an acceptable or non-acceptable amount of light.

7. The system of claim 6 wherein said sensor gives a high or low level alarm representing a non-acceptable solution; the range between said high or low level alarm being an acceptable polymer content for said solution, said alarm being given in response to the amount of light that is detected by said sensor.

8. The system of claim 6 and means responsive to either said high or said low level alarm for shutting down said system.

9. The system of either claim 1 or claim 8 and means jointly responsive to an adjustment of said system to respond to said detected light for displaying a digital signal identifying a level of detected light at which said alarm is given.

10. The system of claim 9 and means for adjusting said displayed digital signal for giving a base line signal in the presence of said electrolyte with no polymer present, and means for readjusting said system from said base line signal to a midscale in said range of acceptable polymer.

11. A system for process polymer comprising a source of neat polymer, a source of electrolyte, means for mixing said polymer with said electrolyte in order to make a solution of activated polymer, optical means for measuring a passage of light through said solution, means for giving a high-low alarm signal if said solution moves outside of an acceptable range, means for initially adjusting said light measuring means to give a first low alarm signal responsive to an optical measurement when said light passes through pure electrolyte, means for adjusting said light measuring means to give a second low alarm signal responsive to a desired polymer concentration in said optical means, and means for adjusting said sources of neat polymer and electrolyte to cause said optical means to give a midscale non-alarm response to one-half of the sum of said first and second low alarm signal levels.

12. The system of claim 11 and a housing for said solution of polymer and electrolyte to pass through a light source on one side of and directed through said housing, a photocell on the other side of and position to receive said light after passing through said housing and any of said solution therein.

13. The system of claim 12 and means for directing all of said solution through said housing.

14. The system of claim 12 and means for diverting some of said solution through said housing.

15. The system of claim 11 wherein said means for mixing to make said solution comprises means for mixing said polymer and electrolyte at a relatively high pressure, and means for suddenly reducing said high pressure in order to relax molecules of said polymer, said optical means being coupled into said system to measure said solution before said sudden reduction of said high pressure.

16. The system of claim 11 wherein said means for mixing in order to make said solution comprises means for mixing said polymer and electrolyte at a relatively high pressure, and means for suddenly reducing high pressure in order to relax molecules of said polymer, said optical means being coupled into said system to measure said solution after said sudden reduction of said high pressure.

* * * * *